(12) United States Patent
Lee et al.

(10) Patent No.: US 12,053,234 B2
(45) Date of Patent: Aug. 6, 2024

(54) SURGICAL NAVIGATION INSTRUMENT HAVING NEEDLE ELECTRODE DEPTH ADJUSTING STRUCTURE FOR DETECTING IMPEDANCE AND HIGH FREQUENCY ENERGY CONTROL METHOD USING SAME

(71) Applicant: CHUNGWOO MEDICAL CO., LTD., Seoul (KR)

(72) Inventors: Il-Kwon Lee, Anyang-si (KR); Kee-Seok Lee, Seoul (KR); Jong-Jun Yim, Gwangmyeong-si (KR)

( * ) Notice: Subject to any disclaimer, the term of this patent is extended or adjusted under 35 U.S.C. 154(b) by 371 days.

(21) Appl. No.: 17/546,533

(22) Filed: Dec. 9, 2021

(65) Prior Publication Data

US 2023/0157746 A1    May 25, 2023

(30) Foreign Application Priority Data

Nov. 24, 2021   (KR) ........................ 10-2021-0163571

(51) Int. Cl.
*A61B 18/14*      (2006.01)
*A61M 1/00*      (2006.01)
(Continued)

(52) U.S. Cl.
CPC ........... *A61B 18/1477* (2013.01); *A61M 1/79* (2021.05); *A61B 2017/00115* (2013.01);
(Continued)

(58) Field of Classification Search
CPC ............ A61B 18/1402; A61B 18/1477; A61B 2017/00026; A61B 2017/00115;
(Continued)

(56) References Cited

U.S. PATENT DOCUMENTS 7,278,991 B2 * 10/2007 Morris ............... A61B 18/1477
606/41
7,824,394 B2 * 11/2010 Manstein ........... A61B 18/1477
606/49
(Continued)

FOREIGN PATENT DOCUMENTS

KR    10-2011-0023494 A    3/2011
KR    10-2013-0142039 A    12/2013
(Continued)

*Primary Examiner* — Michael F Peffley
(74) *Attorney, Agent, or Firm* — KORUS Patent, LLC; Seong Il Jeong

(57) ABSTRACT

Disclosed herein are a surgical navigation instrument having a needle electrode depth adjusting structure for detecting impedance and a high frequency energy control method using the same. The present invention can detect impedance of tissues while applying a pilot signal to an electrode of a high frequency needle according to impedance conditions of the tissues to detect impedance of the tissues, and determine an applied amount of high frequency energy output to high frequency needles according to the detected impedance, thereby reducing patients' pains, maximizing treatment effect, and reducing treatment time according to high frequency energy applied to various depths at the same treatment point when performing a surgical procedure with the same or different treatment parameters according to disease symptoms while selecting the insertion number of high frequency needles, which can be adjusted in penetration depth, into the skin.

18 Claims, 9 Drawing Sheets

(51) Int. Cl.
*A61B 17/00* (2006.01)
*A61B 18/00* (2006.01)

(52) U.S. Cl.
CPC .............. *A61B 2017/00862* (2013.01); *A61B 2018/0016* (2013.01); *A61B 2018/0047* (2013.01); *A61B 2018/00875* (2013.01); *A61B 2018/00922* (2013.01); *A61B 2218/007* (2013.01)

(58) Field of Classification Search
CPC ........... A61B 2017/00747; A61B 2017/00862; A61B 2018/0016; A61B 2018/00291; A61B 2018/0047; A61B 2018/00642; A61B 2018/00666; A61B 2018/00702; A61B 2018/00738; A61B 2018/00875; A61B 2018/0091; A61B 2018/00922; A61B 2018/1475; A61B 2090/062; A61B 2090/064; A61B 2218/007; A61M 1/79
See application file for complete search history.

(56) References Cited

U.S. PATENT DOCUMENTS

| | | | |
|---|---|---|---|
| 8,845,630 B2* | 9/2014 | Mehta | A61B 18/1206 606/41 |
| 10,238,812 B2* | 3/2019 | Ignon | A61B 17/545 |
| 2019/0059992 A1* | 2/2019 | Ko | A61B 18/1477 |
| 2019/0262066 A1* | 8/2019 | Ko | A61B 18/14 |
| 2021/0205005 A1* | 7/2021 | Ko | A61B 18/1206 |
| 2022/0054189 A1* | 2/2022 | Wootten | A61B 18/14 |

FOREIGN PATENT DOCUMENTS

| | | |
|---|---|---|
| KR | 10-2018-0111203 A | 10/2018 |
| KR | 10-2020-0108634 A | 9/2020 |
| KR | 10-2021-0034879 A | 3/2021 |

* cited by examiner

SURGICAL NAVIGATION INSTRUMENT HAVING NEEDLE ELECTRODE DEPTH ADJUSTING STRUCTURE FOR DETECTING IMPEDANCE AND HIGH FREQUENCY ENERGY CONTROL METHOD USING SAME

BACKGROUND OF THE INVENTION

Field of the Invention

The present invention relates to a surgical navigation instrument, and more particularly, to a surgical navigation instrument having a needle electrode depth adjusting structure for detecting impedance and a high frequency energy control method using the same, which can detect impedance of tissues while applying a pilot signal to an electrode of a high frequency needle according to impedance conditions of the tissues to detect impedance of the tissues, and determine an applied amount of high frequency energy output to high frequency needles according to the detected impedance.

Background Art

Surgical devices for applying high frequency energy by skin regeneration and stimulation, skin wrinkle care, or needle insertion into skin through the epidermis in order to improve skin are known in the relevant fields.

For example, Korean Patent Publication No. 10-2013-0142039 discloses a high frequency skin treatment device which can enhance treatment effect by maintaining a constant depth of a needle.

Moreover, Korean Patent Publication No. 10-2011-0023494 discloses a skin care device using high frequency, which can activate cellular tissues and reduce skin aging by directly delivering high frequency current to the dermis between the epidermis and the layer of fat.

Such high frequency treatment devices can be applied to various parts of the human body.

However, in the case that the conventional high frequency treatment devices are applied around the eyes or to the nose or the neck, the conventional high frequency treatment devices have several disadvantages in that it is difficult to insert a plurality of needles to uniform depth or in a fixed direction, and in that it is also difficult to make the needles penetrate tissues.

Furthermore, it is necessary to improve treatment effect by penetrating the high frequency needles to various depths at the same position. Therefore, such high frequency needle devices have to have means which can make needles penetrate tissues regardless of parts of the human body and insert the needles to a fixed depth. Additionally, the high frequency treatment devices have to have a structure capable of applying high frequency to various depths.

However, conventional arts or known arts do not disclose a high frequency needle treatment device having the above-mentioned functions.

PATENT LITERATURE

Patent Documents

Patent Document 1: Korean Patent Publication No. 10-2011-0023494 (published on Mar. 8, 2011)
Patent Document 2: Korean Patent Publication No. 10-2013-0142039 (published on Dec. 27, 2013)

SUMMARY OF THE INVENTION

Accordingly, the present invention has been made to solve the above-mentioned problems occurring in the prior arts, and it is an object of the present invention to provide a surgical navigation instrument having a needle electrode depth adjusting structure for detecting impedance and a high frequency energy control method using the same, which can detect impedance of tissues while applying a pilot signal to an electrode of a high frequency needle according to impedance conditions of the tissues to detect impedance of the tissues, and determine an applied amount of high frequency energy output to high frequency needles according to the detected impedance, thereby reducing patients' pains, maximizing treatment effect, and reducing treatment time according to high frequency energy applied to various depths at the same treatment point when performing a surgical procedure with the same or different treatment parameters according to disease symptoms while selecting the insertion number of high frequency needles, which can be adjusted in penetration depth, into the skin.

To accomplish the above object, according to the present invention, there is provided a surgical navigation instrument having a needle electrode depth adjusting structure for detecting impedances including: a needle module having a plurality of high frequency needles which are inserted into tissues to be treated; a handpiece to which the needle module is coupled; an impedance detection unit connected to electrodes of the high frequency needles through the handpiece, and detects the impedance of the tissues while applying pilot signals for detecting impedance to the electrodes 11a of the high frequency needles; and a control unit connected to the needle module through the handpiece and adjusts the high frequency needles to have the same or different penetration depths to the tissues according to setting signals input through a setting input unit so the same or different high frequency energies applied to the high frequency needles are controlled according to the impedance detected from the impedance detection unit.

Moreover, the impedance detection unit, the control unit, and the setting input unit are disposed in a surgical body, and an impedance reference table that determines an application amount of high frequency energy to be output according to the impedance of the tissue detected by the impedance detection unit is stored in the control unit.

Furthermore, the setting input unit is a touch panel mounted on the surgical body, and displays a preset treatment mode and a manual treatment mode controlled by the control unit.

Additionally, the setting input unit in the preset treatment mode includes: an indication setting button; a treated area setting button; a needle parameter setting button for setting treatment parameters of the high frequency needles; a parameter initialization button for restoring an initial value when treatment parameters of the high frequency needles are changed by the needle parameter setting button; a suction on/off button for selecting activation and inactivation of a suction function in relation to the treated area or indications which does not need the suction function; a needle cleaning button for maximizing forward movement of the high frequency needles in order to clean biological tissues attached to the high frequency needles during the treatment; a suction pressure display unit for visually displaying the level of suction pressure in the range from 0% to 100% based on the threshold value in order to induce correction of a treatment posture and a treatment method in relation to the high frequency needles providing the suction function; and a needle display unit for displaying kinds of the high frequency needles.

In addition, the setting input unit in the manual treatment mode includes: a needle parameter setting button for setting treatment parameters of the high frequency needles; a treatment parameter setting button for allowing a user to select the same or different treatment parameters according to indications and treated areas; a shot number setting button for selecting the insertion number of the high frequency needles according to parameters set by the needle parameter setting button and the treatment parameter setting button; a parameter initialization button for restoring an initial value when treatment parameters of the high frequency needles and parameters set by the user are changed by the needle parameter setting button and the treatment parameter setting button; a suction on/off button for selecting activation and inactivation of a suction function in relation to the treated area or indications which does not need the suction function; a needle cleaning button for maximizing forward movement of the high frequency needles in order to remove malfunction of the high frequency needles or to clean biological tissues attached to the high frequency needles during the treatment; a suction pressure display unit for visually displaying the level of suction pressure in the range from 0% to 100% based on the threshold value in order to induce correction of a treatment posture and a treatment method in relation to the high frequency needles providing the suction function; and a needle display unit for displaying kinds of the high frequency needles.

Moreover, the control unit controls the high frequency needles to automatically move forwards when suction pressure displayed on the suction pressure display unit reaches the threshold value.

Furthermore, the handpiece has a filter case in which a filter having a buffer is accommodated in order to filter biological materials generated during treatment.

Additionally, the high frequency needles are arranged to be uniformly distributed on the needle module having a rectangular or circular cross-section.

In addition, each of the high frequency needles has depth ranging from 5 mm to 20 mm, and transmits radio frequency energy ranging from 1 MHz to 20 MHz after being penetrated into skin tissues to depth ranging from 0.5 mm to 9 mm.

Moreover, the needle module includes a driving unit for positioning the plurality of high frequency needles at different penetration depths and detecting the movement depth of the high frequency needles into the tissues to be treated.

Furthermore, the needle module includes an adjusting substrate on which the plurality of high frequency needles are arranged, and the adjusting substrate is vertically moved by movement of a pair of adjustable shafts connected to the driving unit.

Additionally, the driving unit detects the vertical movement of the adjusting shafts and pressure applied to the adjusting shafts, and also detects the penetration depth of the high frequency needles.

In addition, the needle module further includes: a contact cap which accommodates the adjusting substrate on which the high frequency needles are arranged, which has a circular contact rim on a contact surface getting in contact with the skin and is joined to the handpiece, the contact tap having an induction tap which induces gas from the outside or discharges gas to the outside; a pair of elastic parts which are accommodated in the contact cap to relieve shock caused by penetration of the high frequency needles and limit the penetration depth of the high frequency needles; and a limiting part to which the elastic parts are joined, and the adjusting substrate is accommodated in the limiting part.

Moreover, the driving unit detects elastic force applied from the elastic parts to detect penetration depth and penetration pressure of the high frequency needles.

Furthermore, the needle module further includes a plurality of absorption parts arranged on the peripheral surface thereof, and the absorption parts are arranged to surround the adjusting substrate.

Additionally, a contact part getting in contact with the skin is formed at the front portion of the contact cap, and the absorption parts are formed at the contact part and are connected with the induction tap formed on the side of the contact cap.

In addition, the absorption part has a contact block and a plurality of suction holes formed in the contact block, and the suction holes are connected with the induction tap so that gas flows therebetween.

Moreover, the needle module includes: a locking part accommodated in a housing of the handpiece to lock or unlock the operation of the driving unit and to connect the high frequency needles to the driving unit; and an output connector for transmitting high frequencies to the high frequency needles.

Furthermore, the control unit includes: a penetration depth control unit for adjusting the operation of the driving unit; an applied energy control unit for applying the same or different high frequency energies to the high frequency needles at different depths according to the signal transmitted from the driving unit; and a control unit for controlling movement of the high frequency needles and the operation of the penetration depth control unit on the basis of detection information of the driving unit, controlling the operation of the applied energy adjusting unit according to impedance information detected by the impedance detection unit in order to determine high frequency energy applied from the same and different penetration depths of the high frequency needles.

In another aspect of the present invention, there is provided a high frequency energy control method using a surgical navigation instrument having a needle electrode depth adjusting structure for detecting impedance, the high frequency energy control method including: a first step of making high frequency needles penetrate tissues to be treated; a second step of applying a pilot signal for detecting impedance to the electrodes of the high frequency needles penetrated into the tissues, and detecting initial impedance of the tissues; a third step of determining whether the detected initial impedance detected in the second step corresponds to a set initial impedance value; a fourth step of, if the determined initial impedance does not correspond to the set impedance value, finishing the surgical treatment relative to the tissues, but if the detected initial impedance corresponds to the set initial impedance value, applying high frequency energy to the electrodes of the high frequency needles; a fifth step of periodically re-detecting impedance changing according to high frequency energy applied to the high frequency needles; a sixth step of determining whether the changing impedance periodically re-detected corresponds to a set target impedance value for treatment of the tissues; and a seventh step of, if the re-detected impedance does not correspond to the set target impedance value, repeating the application of high frequency energy to the high frequency needles, but if the re-detected impedance corresponds to the set target impedance value, finishing the surgical treatment relative to the tissues.

Additionally, in the sixth step, the high frequency energy control method further includes a step of controlling the application amount of high frequency energy according to the impedance periodically detected, and determining the position and condition of the tissues, whether there is any error in the electrodes of the high frequency needles 11, whether the high frequency needles 11 reach the treatment positions of the tissues, whether preparation for the surgical operation is completed, whether high frequency energy is applied, and whether the surgical treatment relative to the tissues is finished according to detection of the impedance.

According to the present invention, the surgical navigation instrument having a needle electrode depth adjusting structure for detecting impedance and a high frequency energy control method using the same can detect impedance of tissues while applying a pilot signal to an electrode of a high frequency needle according to impedance conditions of the tissues to detect impedance of the tissues, and determine an applied amount of high frequency energy output to high frequency needles according to the detected impedance, thereby reducing patients' pains, maximizing treatment effect, and reducing treatment time according to high frequency energy applied to various depths at the same treatment point when performing a surgical procedure with the same or different treatment parameters according to disease symptoms while selecting the insertion number of high frequency needles, which can be adjusted in penetration depth, into the skin.

The effects of the present invention are not limited to the above-mentioned effects and further effects not described above will be clearly understood by those skilled in the art.

BRIEF DESCRIPTION OF THE DRAWINGS

The above and other objects, features and advantages of the present invention will be apparent from the following detailed description of the preferred embodiments of the invention in conjunction with the accompanying drawings, in which.

DETAILED DESCRIPTION OF THE PREFERRED EMBODIMENT

Hereinafter, embodiments of the present invention will be described in detail with reference to the accompanying drawings.

Figure 1:
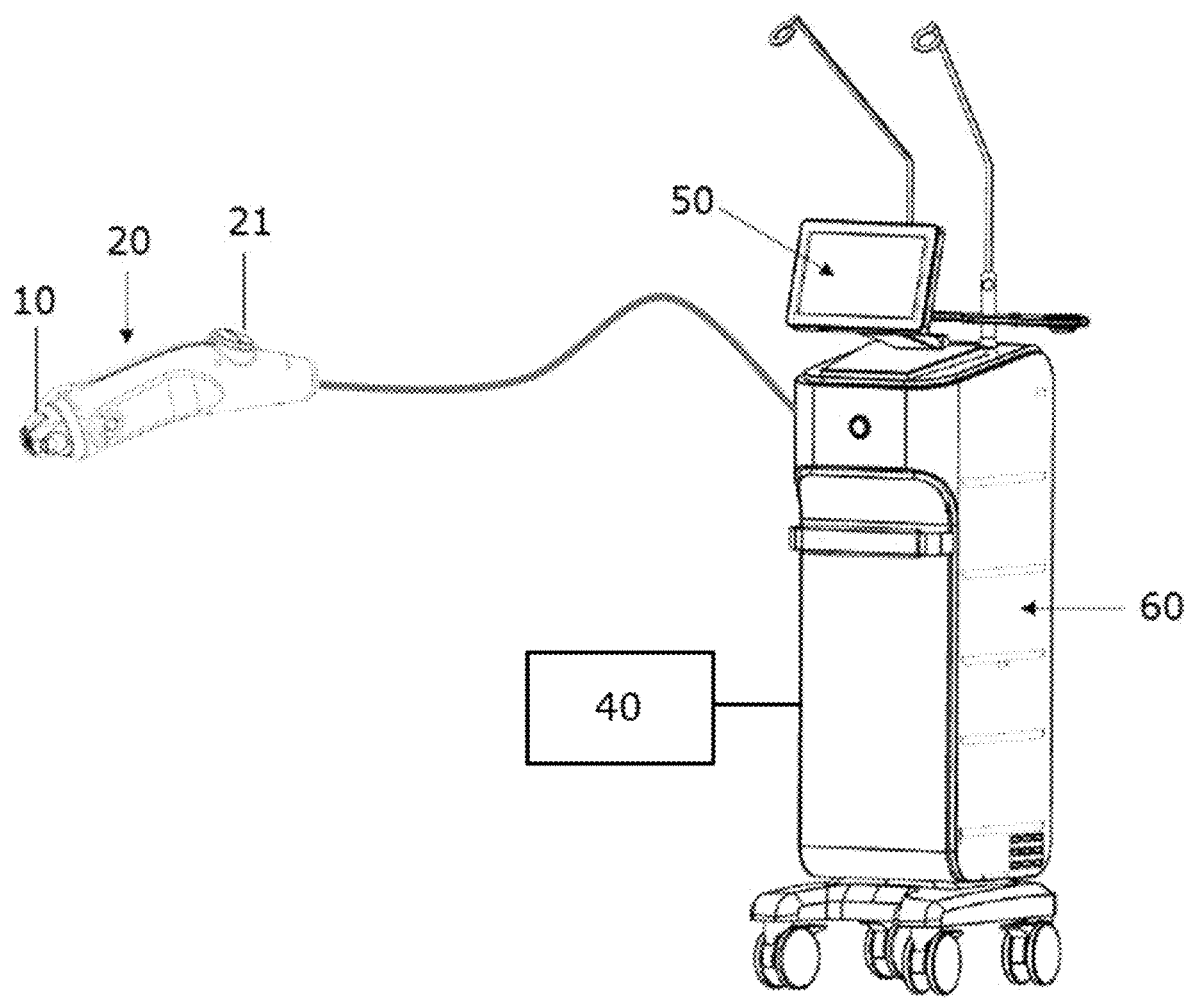
FIG. 1 is a structure diagram of a surgical navigation instrument having a needle electrode depth adjusting structure for detecting impedance according to an embodiment of the present invention.
Figure 2:
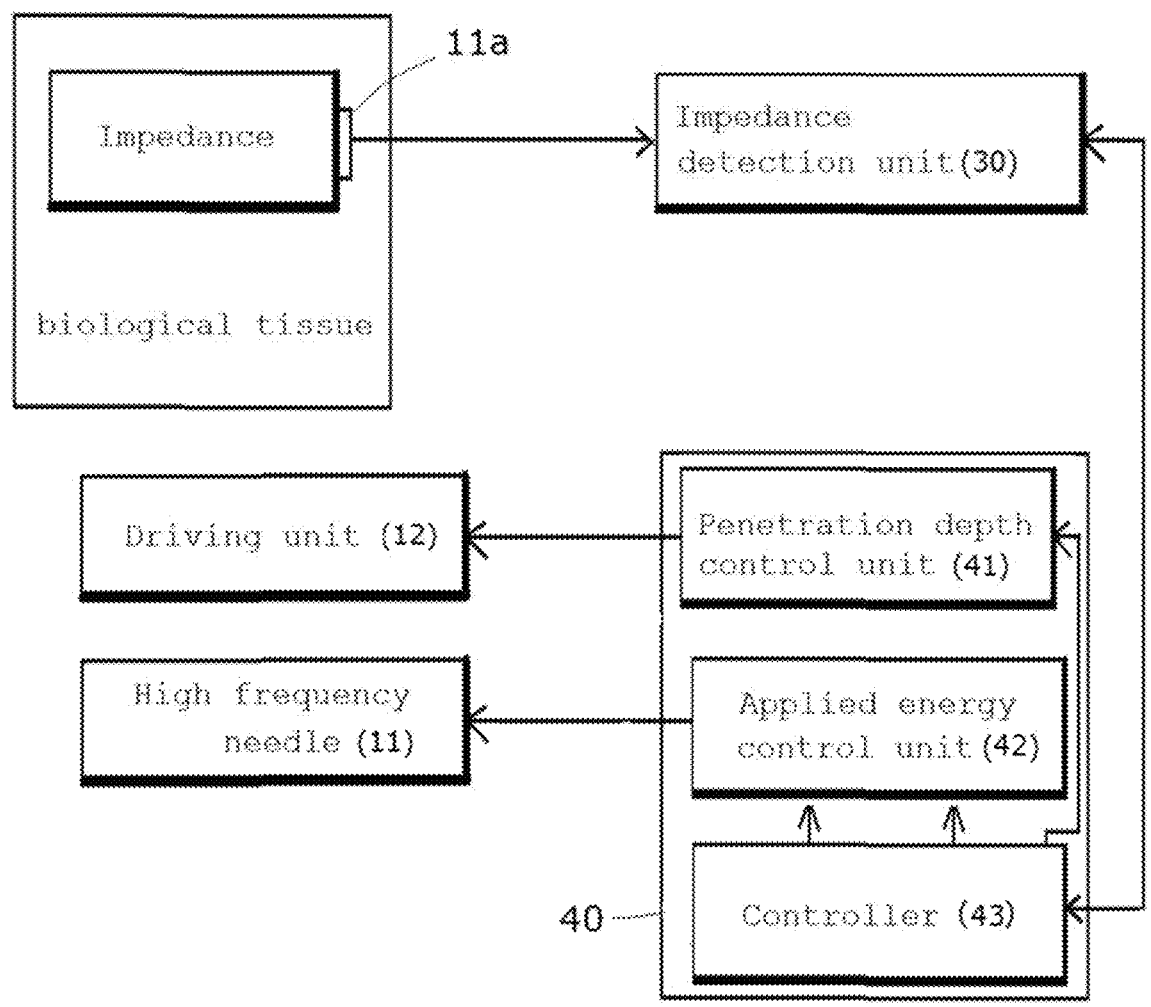
FIG. 2 is a schematic control block diagram of the surgical navigation instrument having the needle electrode depth adjusting structure for detecting impedance according to the embodiment of the present invention.
Figure 3:
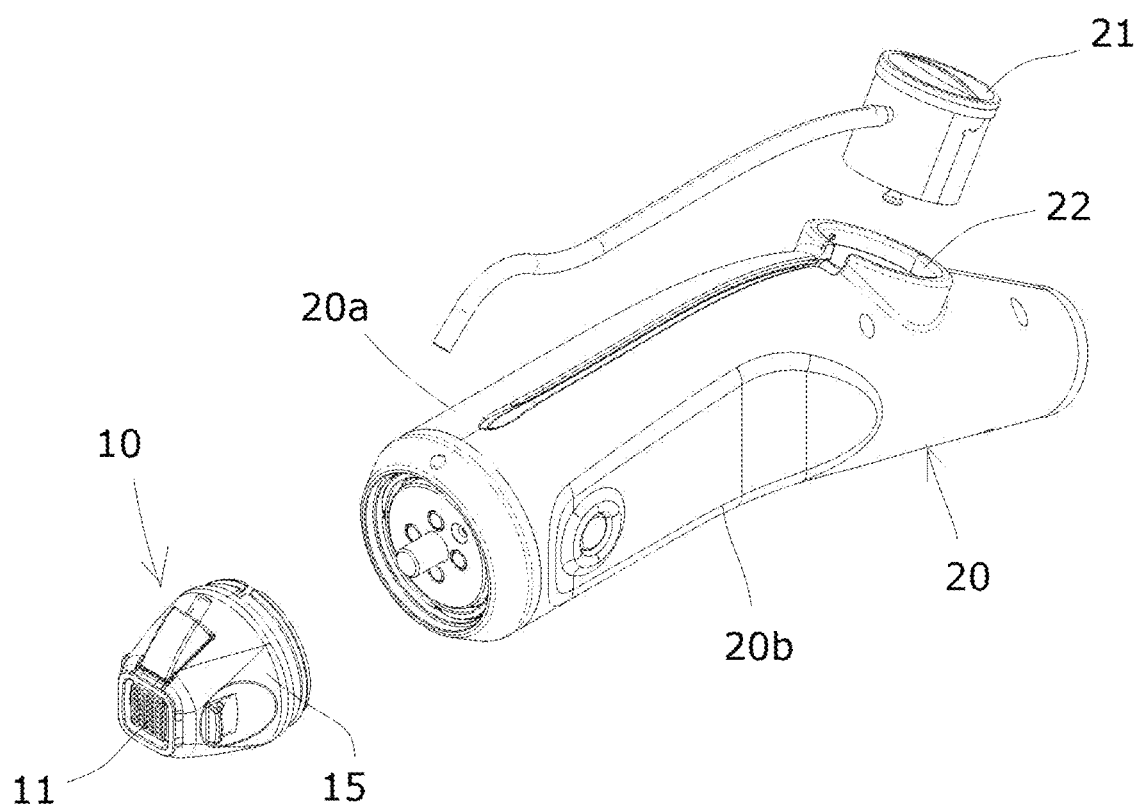
FIGS. 3 and 4 are exploded perspective view of a handpiece and a needle module according to the embodiment of the present invention.
Figure 4:
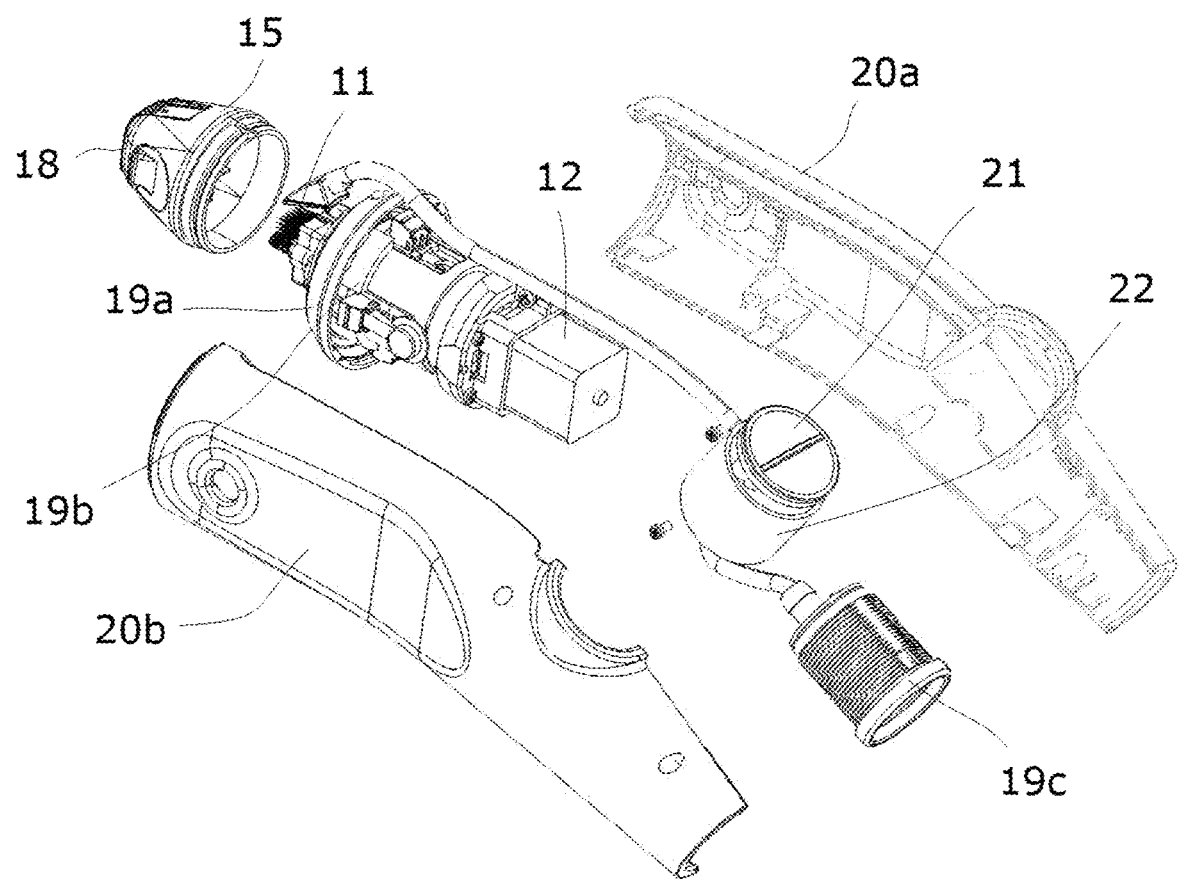
Figure 5:
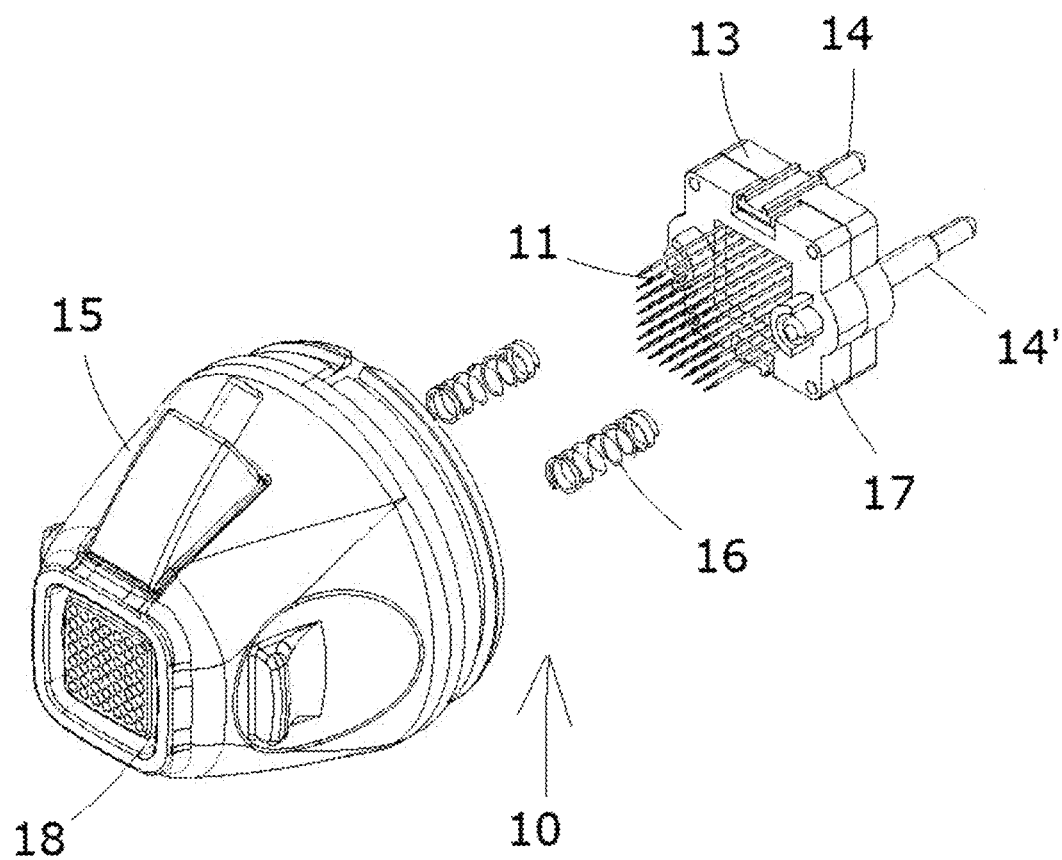
FIGS. 5 and 6 are exploded view illustrating a structure of the needle module according to the embodiment of the present invention.
Figure 6:
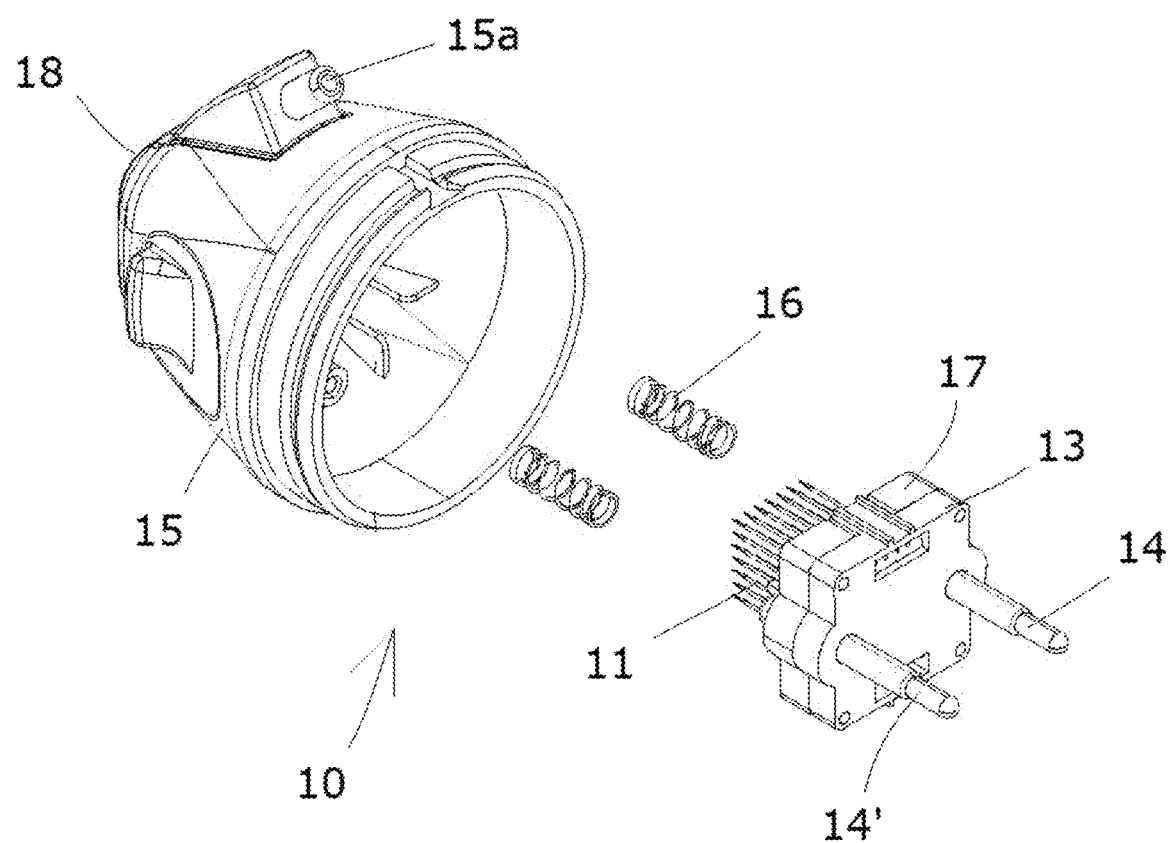

FIG. 1 is a structure diagram of a surgical navigation instrument having a needle electrode depth adjusting structure for detecting impedance according to an embodiment of the present invention, FIG. 2 is a schematic control block diagram of the surgical navigation instrument having the needle electrode depth adjusting structure for detecting impedance according to the embodiment of the present invention, FIGS. 3 and 4 are exploded perspective view of a handpiece and a needle module according to the embodiment of the present invention, and FIGS. 5 and 6 are exploded view illustrating a structure of the needle module according to the embodiment of the present invention.

Referring to FIGS. 1 to 6, the surgical navigation instrument having a needle electrode depth adjusting structure for detecting impedance according to the embodiment of the present invention includes a needle module 10, a handpiece 20, an impedance detection unit 30, a control unit 40, a setting input unit 50, and a surgical body 60.

The needle module 10 includes a plurality of high frequency needles 11 having a rectangular or circular cross-section, which is inserted into tissues.

Here, the high frequency needle 11 may have depth of 5 mm to 20 mm, and can transmit radio frequency energy of 1 MHz to 20 MHz after being penetrated into skin tissues to depth ranging from 0.5 mm to 9 mm, but is not limited to the above.

The high frequency needle 11 can be moved to be adjusted in penetration depth by a driving unit 12, such as a motor. The plurality of high frequency needles 11 must penetrate tissues while moving at the same time. However, according to tissues, it may be difficult that the high frequency needles 11 penetrate the tissues or the high frequency needles 11 do not penetrate uniformly according to shapes of the tissues. Moreover, in spite of general tissues, it is advantageous to make the high frequency needles 11 easily penetrate the tissues. For this, a plurality of absorption parts 18 are arranged on the peripheral surface of the high frequency needles 11. The absorption parts 18 may have a structure of surrounding the high frequency needles 11 or have a shape to apply pressure to a contact part getting in contact with the skin.

That is, not shown in the drawings, the absorption part 18 may have five contact parts surrounding the high frequency needles 11 or have one contact part.

The absorption part 18 gets in contact with the skin, for instance, in order to generate negative pressure at the contact part, so that the tissues may be formed into a concave groove or a similar shape while the tissues which the high frequency needles 11 penetrate are pulled in the direction of the absorption part 18. Therefore, the high frequency needles 11 can penetrate the tissues easily and uniformly.

Here, the needle module 10 is combined with the handpiece 20 having a plurality of housings 20a and 20b, and a contact cap 15 of the needle module 10 is coupled to one end of the handpiece 20.

Meanwhile, the plurality of high frequency needles 11 can be adjusted in penetration depth while the driving unit 12, such as a stepping motor, detects a movement depth. Accordingly, the plurality of high frequency needles 11 is arranged on an adjusting substrate 13, the adjusting substrate 13 is vertically moved by movement of a pair of adjustable shafts 14 and 14' so that the plurality of high frequency needles 11 can be moved vertically.

The driving unit 12 can detect the vertical movement of the adjustable shafts 14 and 14', and at the same time, detect pressure applied to the adjustable shafts 14 and 14'. The driving unit 12 can confirm a penetrated state by detecting the penetration depth according to the movement of the adjustable shafts 14 and 14' and pressure applied to the adjustable shafts 14 and 14'. Furthermore, detection information is transmitted to the control unit 40, and the control module 40 can adjust movement of the high frequency needles 11 based on the detection information.

In the meantime, the high frequency needles 11 can be accommodated in the contact cap 15, and the contact cap 15 includes an induction tap 15a which forms a circular contact rim on a contact surface getting in contact with the skin and induces gas from the outside or discharges gas to the outside. A pair of elastic parts 16 and a limiting part 17 to which the elastic parts 16 are joined are arranged on the contact cap 15.

The adjusting substrate 13 is accommodated inside the limiting part 17, and the elastic parts 16 can relieve shock caused by penetration of the high frequency needles 11 and limit the penetration depth of the high frequency needles 11. The driving unit 12 detects elastic force applied from the elastic part 16 in order to detect the penetration depth and penetration pressure of the high frequency needles 11.

Here, the high frequency needles 11 may have various structures, such as a 14-pin structure, a 25-pin structure, a 36-pin structure, or a 49-pin structure, and the absorption part 18 may have one of various structures surrounding the high-frequency needle 11, and is not limited to the proposed embodiment.

Moreover, the needle module 10 includes: a locking part 19b for connecting the high frequency needles 11 with the driving unit 12 while locking or unlocking the operation of the driving unit 12; and an output connector 19c for transmitting high frequencies to the high frequency needles 11. The locking part 19b and the output connector 19c are accommodated in the handpiece 20.

The handpiece 20 is formed by coupling of a plurality of accommodation housings 20a and 20b and is connected with the surgical body 60 via a cable. A filter case 22 is accommodated in the handpiece 20, and a filter 21 having a buffer is accommodated in the filter case 22 in order to filter biological materials, such as blood, generated during treatment.

Here, for instance, one end of the filter 21 is connected to a suction pump installed in an operation module, and the other end of the filter 21 is connected to the induction tap 15a. The induction tap 15a is formed on the outer circumferential surface of the contact cap 15 to be connected to the absorption part 18. The contact cap 15 is detachably disposed at the front of the handpiece 20 by a coupling connector 19a, and the high frequency needles 11 are arranged inside the contact cap 15.

Therefore, the surgical navigation instrument according to the embodiment of the present invention allows the needles to penetrate the skin regardless of skin characteristics or structure since an absorption area is formed around the tissues according to negative pressure. The surgical navigation instrument according to the present invention allows needles to easily penetrate the skin of various parts of the body, for instance, including areas where the needles are difficult to be inserted, such as around the eyes, the nose or the neck.

The impedance detection unit 30 is connected to electrodes 11a of the high frequency needles 11 through the handpiece 20, and detects the impedance of the tissues while applying pilot signals for detecting impedance to the electrodes 11a of the high frequency needles 11.

The control unit 40 is connected to the needle module 10 through the handpiece 20 and adjusts the high frequency needles 11 to have the same or different penetration depths to the tissues according to setting signals input through a setting input unit 50. That is, the control unit 40 can adjust the same or different high frequency energies applied to the high frequency needles 11 according to the impedance detected from the impedance detection unit 30.

Therefore, an impedance reference table (not shown) that determines an application amount of high frequency energy to be output according to the impedance of the tissue detected by the impedance detection unit 30 is stored in the control unit 40.

That is, a controller 43 included in the control unit 40 can adjust operations of a penetration depth control unit 41 and an applied energy control unit 42 according to the impedance detected by the impedance detection unit 30 so as to determine the penetration depth of the high frequency needles 11 and high frequency energy applied from the different penetration depths, to set at least two penetration depths in the tissues, and to determine the level of the high frequency energy applied from each penetration depth.

In detail, the penetration depth control unit 41 of the control unit 40 adjusts the operation of the driving unit 12, and the applied energy control unit 42 applies the same or different high frequency energies to the high frequency needles 11 at different depths according to the signal transmitted from the driving unit 12. The controller 43 controls movement of the high frequency needles 11, and operations of the penetration depth control unit 41 and the applied energy control unit 42 on the basis of detection information of the driving unit 12 in order to determine high frequency energy applied from the same and different penetration depths of the high frequency needles 11. The determination of the high frequency energy can be controlled according to the impedance detected by the impedance detection unit 30.

Figure 9:
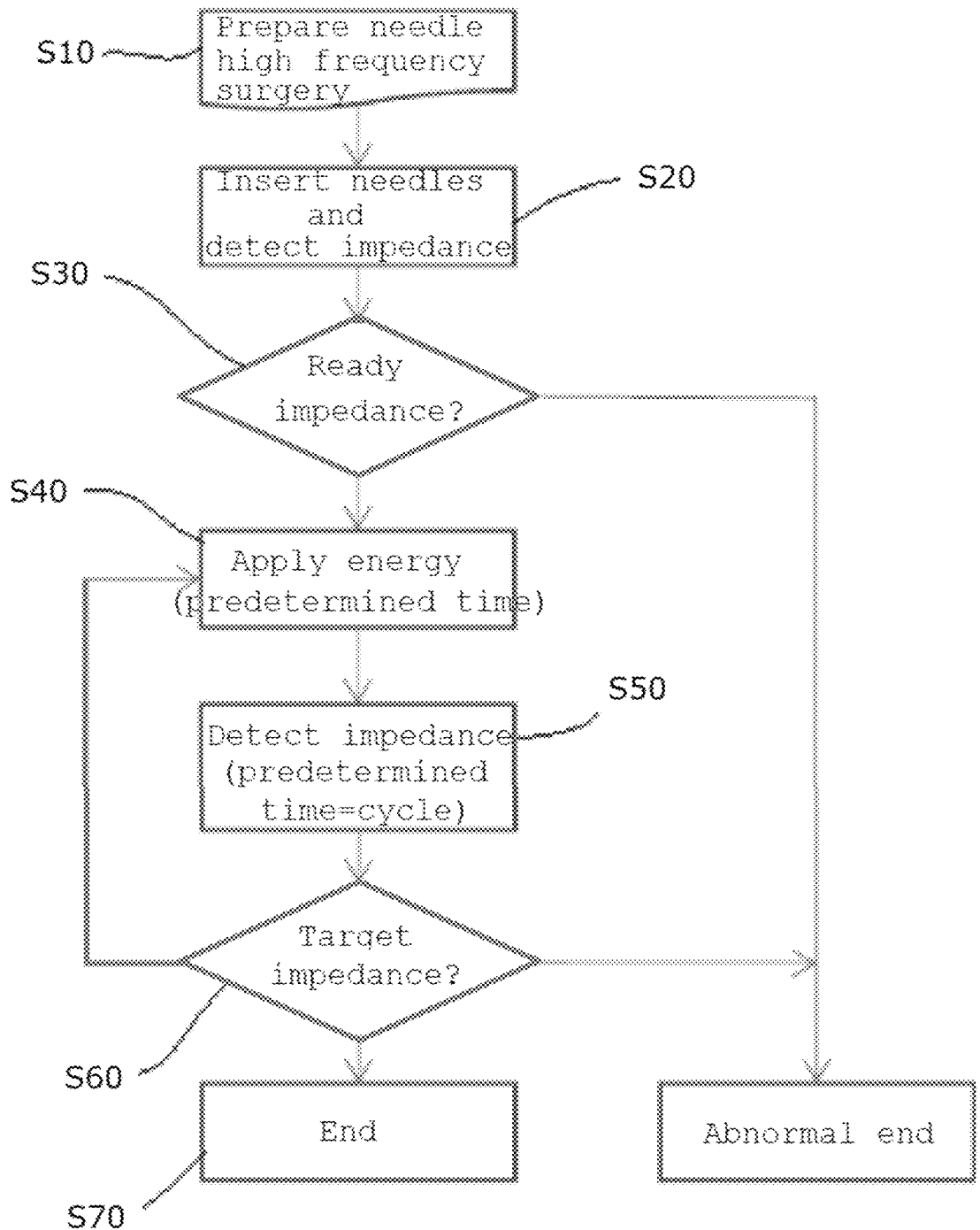
FIG. 9 is a flow chart illustrating a high frequency energy control method using a surgical navigation instrument having a needle electrode depth adjusting structure for detecting impedance.

That is, as illustrated in FIG. 9, when the high frequency needles 11 are penetrated into the tissues to be treated (S10), the impedance detection unit 30 applies a pilot signal for detecting impedance to the electrodes 11a of the high frequency needles 11 penetrated into the tissues, detects initial impedance of the tissues, and outputs the detected impedance to the controller 43 (S20).

Then, the controller 43 determines whether the detected initial impedance corresponds to a set initial impedance value (Z). If the determined initial impedance does not correspond to the set impedance value (Z), the surgical treatment relative to the tissues is finished. If the detected initial impedance corresponds to the set initial impedance value (Z), the applied energy control unit 42 is controlled so that high frequency energy is applied to the electrodes 11a of the high frequency needles 11 (S40).

Meanwhile, when high frequency energy is applied to the high frequency needles 11 by the applied energy control unit 42, the impedance detection unit 30 periodically re-detects impedance changing according to high frequency energy applied to the high frequency needles 11 for a predetermined period of time, and outputs the detected impedance to the controller 43 (S50).

Then, the controller 43 determines whether the changing impedance periodically re-detected corresponds to a set target impedance value (Z') for treatment of the tissues (S60). As a determination result, if the re-detected impedance does not correspond to the set target impedance value (Z'), the application of high frequency energy to the high frequency needles 11 through the applied energy control unit 42 is repeated, but if the re-detected impedance corresponds to the set target impedance value (Z'), the surgical treatment relative to the tissues is finished (S70).

Here, the controller 43 can control the application amount of high frequency energy to the high frequency needles 11 through the applied energy control unit 42 according to the impedance periodically detected by the impedance detection unit 30, and determine the position and condition of the tissues, whether there is any error in the electrodes of the high frequency needles 11, whether the high frequency needles 11 reach the treatment positions of the tissues, whether preparation for the surgical operation is completed, whether high frequency energy is applied, and whether the surgical treatment relative to the tissues is finished according to detection of the impedance.

On the other hand, the setting input unit 50 is a touch panel for displaying a treatment condition when the treatment is performed according to treatment conditions set by a user, and the touch panel displays a preset treatment mode and a manual treatment mode controlled by the control unit 40.

Figure 7:
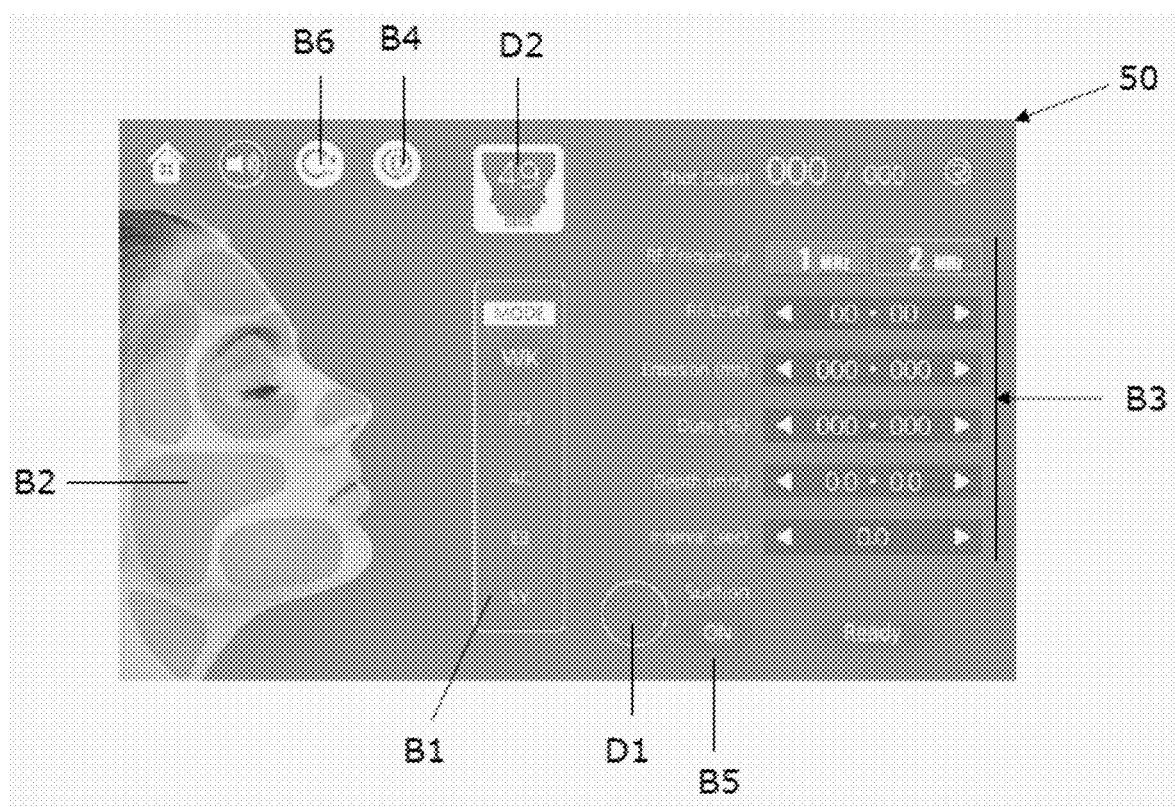
FIG. 7 is a screen view illustrating a state in which a preset treatment mode is displayed on a setting input unit.

That is, as illustrated in FIG. 7, the setting input unit 50 in the preset treatment mode includes: an indication setting button B1; a treated area setting button B2; a needle parameter setting button B3 for setting treatment parameters of the high frequency needles 11; a parameter initialization button B4 for restoring an initial value when treatment parameters of the high frequency needles 11 are changed by the needle parameter setting button B3; a suction on/off button B5 for selecting activation and inactivation of a suction function in relation to the treated area or indications which does not need the suction function; a needle cleaning button B6 for maximizing forward movement of the high frequency needles 11 in order to clean biological tissues attached to the high frequency needles 11 during the treatment; a suction pressure display unit D1 for visually displaying the level of suction pressure in the range from 0% to 100% based on the threshold value in order to induce correction of a treatment posture and a treatment method in relation to the high frequency needles 11 providing the suction function; and a needle display unit D2 for displaying kinds of the high frequency needles 11.

Figure 8:
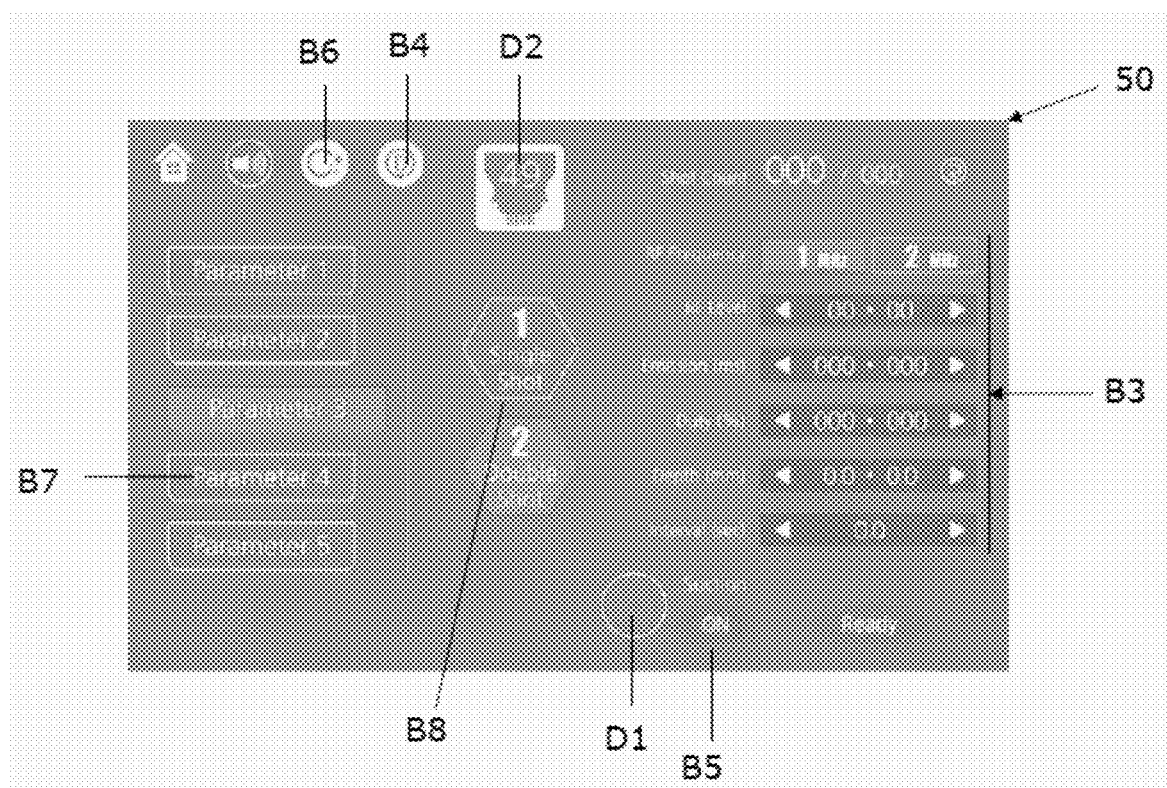
FIG. 8 is a screen view illustrating a state in which a manual treatment mode is displayed on the setting input unit.

On the other hand, as illustrated in FIG. 8, the setting input unit 50 in the manual treatment mode includes: a needle parameter setting button B3 for setting treatment parameters of the high frequency needles 11; a treatment parameter setting button B7 for allowing a user to select the same or different treatment parameters according to indications and treated areas; a shot number setting button B8 for selecting the insertion number of the high frequency needles 11 according to parameters set by the needle parameter setting button B3 and the treatment parameter setting button B7; a parameter initialization button B4 for restoring an initial value when treatment parameters of the high frequency needles 11 and parameters set by the user are changed by the needle parameter setting button B3 and the treatment parameter setting button B7; a suction on/off button B5 for selecting activation and inactivation of a suction function in relation to the treated area or indications which does not need the suction function; a needle cleaning button B6 for maximizing forward movement of the high frequency needles 11 in order to clean biological tissues attached to the high frequency needles 11 during the treatment; a suction pressure display unit D1 for visually displaying the level of suction pressure in the range from 0% to 100% based on the threshold value in order to induce correction of a treatment posture and a treatment method in relation to the high frequency needles 11 providing the suction function; and a needle display unit D2 for displaying kinds of the high frequency needles 11.

Accordingly, the control unit 40 can control treatment by the needle module 10 based on information set in the preset treatment mode or the manual treatment mode displayed on the setting input unit 50. For instance, the control unit 40 controls the high frequency needles 11 to automatically move forwards when suction pressure displayed on the suction pressure display unit D1 reaches the threshold value.

That is, when tissues to be treated is set, the number of times of treatment relative to the tissues is set. The tissues to be treated may be, for instance, a face area, a neck area, or other similar parts of the human body, and the corresponding area is created by scanning.

Meanwhile, when the position of the tissues to be treated is determined, a treatment depth and high frequency energy to be applied are determined according to detection of impedance. Additionally, when suction pressure is set, the plurality of high frequency needles 11 are moved to the tissues at the same or different depths to receive high frequency energy.

In other words, the surgical navigation instrument according to the embodiment of the present invention can provide treatment effects of numerous times by just one treatment since applying high frequency energy at least twice while penetrating the high frequency needles 11 to different depths at one treatment position, thereby minimizing skin damage and providing the same treatment effect as treatments of numerous times by just one treatment or treatment effect more than that. Additionally, the surgical navigation instrument according to the embodiment of the present invention can reduce treatment time, apply different high frequency energies at appropriate depths according to treated areas, and properly control application of the high frequency energies through detection of impedance.

As described above, while the surgical navigation instrument having the needle electrode depth adjusting structure for detecting impedance and the high frequency energy control method using the same according to the present invention has been described with reference to the attached drawings, it will be understood by those of ordinary skill in the art that the above embodiments of the present invention are all exemplified and are not to limit the technical idea of the present invention, and various changes, modifications and equivalents may be made therein without changing the essential characteristics and scope of the present invention. Therefore, it would be understood that the embodiments disclosed in the present invention but to describe the present invention, and the technical and protective scope of the present invention shall be defined by the illustrated embodiments.

While the present invention has been particularly shown and described with reference to exemplary embodiments thereof, it will be understood by those of ordinary skill in the art that various changes, modifications, and equivalents may be made therein without departing from the technical idea and scope of the present invention and such changes, modifications, and equivalents belong to the claims of the present invention.

What is claimed is:

1. A surgical navigation instrument comprising:
    a needle module having a plurality of high frequency needles which are configured to be inserted into tissues to be treated;
    a handpiece to which the needle module is coupled;
    an impedance detection unit connected to electrodes of the high frequency needles through the handpiece, and configured to detect an impedance of the tissues while applying pilot signals for detecting impedance to the electrodes of the high frequency needles; and
    a control unit connected to the needle module through the handpiece and configured to adjust the high frequency needles to have various penetration depths to the tissues according to setting signals input through a setting input unit so high frequency energies applied to the high frequency needles are controlled according to the impedance detected from the impedance detection unit, wherein the setting input unit is a touch panel mounted on a surgical body, and displays a preset treatment mode and a manual treatment mode controlled by the control unit, wherein the setting input unit in the preset treatment mode includes:

an indication setting button; a treated area setting button; a needle parameter setting button for setting treatment parameters of the high frequency needles; a parameter initialization button for restoring an initial value when treatment parameters of the high frequency needles are changed by the needle parameter setting button; a suction on/off button for selecting activation and inactivation of a suction function; a needle cleaning button for maximizing forward movement of the high frequency needles in order to clean biological tissues attached to the high frequency needles during the treatment; and a suction pressure display unit for visually displaying the level of suction pressure in the range from 0% to 100% based on a threshold value in order to induce correction of a treatment posture and a treatment method in relation to the high frequency needles providing the suction function.

2. The surgical navigation instrument according to claim 1, wherein the impedance detection unit, the control unit, and the setting input unit are disposed in the surgical body, and an impedance reference table that determines an application amount of high frequency energy to be output according to the impedance of the tissue detected by the impedance detection unit is stored in the control unit.

3. The surgical navigation instrument according to claim 1, wherein the control unit controls the high frequency needles to automatically move forwards when suction pressure displayed on the suction pressure display unit reaches the threshold value.

4. The surgical navigation instrument according to claim 1, wherein the handpiece has a filter case in which a filter having a buffer is accommodated in order to filter biological materials generated during treatment.

5. The surgical navigation instrument according to claim 1, wherein the high frequency needles are arranged to be uniformly distributed on the needle module having a rectangular or circular cross-section.

6. The surgical navigation instrument according to claim 1, wherein each of the high frequency needles has depth ranging from 5 mm to 20 mm, and transmits radio frequency energy ranging from 1 MHz to 20 MHz after being penetrated into skin tissues to depth ranging from 0.5 mm to 9 mm.

7. The surgical navigation instrument according to claim 1, wherein the needle module includes a driving unit for positioning the plurality of high frequency needles at different penetration depths and detecting the movement depth of the high frequency needles into the tissues to be treated.

8. The surgical navigation instrument according to claim 7, wherein the needle module includes an adjusting substrate on which the plurality of high frequency needles are arranged, and the adjusting substrate is vertically moved by movement of a pair of adjustable shafts connected to the driving unit.

9. The surgical navigation instrument according to claim 8, wherein the driving unit detects the vertical movement of the adjusting shafts and pressure applied to the adjusting shafts, and also detects the penetration depth of the high frequency needles.

10. The surgical navigation instrument according to claim 9, wherein the needle module further comprises:

a contact cap which accommodates the adjusting substrate on which the high frequency needles are arranged, which has a circular contact rim on a contact surface getting in contact with the skin and is joined to the handpiece, the contact tap having an induction tap which induces gas from the outside or discharges gas to the outside;

a pair of elastic parts which are accommodated in the contact cap to relieve shock caused by penetration of the high frequency needles and limit the penetration depth of the high frequency needles; and a limiting part to which the elastic parts are joined, and wherein the adjusting substrate is accommodated in the limiting part.

11. The surgical navigation instrument according to claim 10, wherein the driving unit detects elastic force applied from the elastic parts to detect penetration depth and penetration pressure of the high frequency needles.

12. The surgical navigation instrument according to claim 11, wherein the needle module further comprises a plurality of absorption parts arranged on the peripheral surface thereof, and the absorption parts are arranged to surround the adjusting substrate.

13. The surgical navigation instrument according to claim 12, wherein a contact part getting in contact with the skin is formed at the front portion of the contact cap, and the absorption parts are formed at the contact part and are connected with the induction tap formed on the side of the contact cap.

14. The surgical navigation instrument according to claim 13, wherein the absorption part has a contact block and a plurality of suction holes formed in the contact block, and the suction holes are connected with the induction tap so that gas flows therebetween.

15. The surgical navigation instrument according to claim 14, wherein the needle module comprises: a locking part accommodated in a housing of the handpiece to lock or unlock the operation of the driving unit and to connect the high frequency needles to the driving unit; and an output connector for transmitting high frequencies to the high frequency needles.

16. The surgical navigation instrument according to claim 7, wherein the control unit comprises:

a penetration depth control unit for adjusting the operation of the driving unit;

an applied energy control unit for applying the high frequency energies to the high frequency needles at different depths according to the signal transmitted from the driving unit; and a control unit for controlling movement of the high frequency needles and the operation of the penetration depth control unit on the basis of detection information of the driving unit, controlling the operation of the applied energy adjusting unit according to impedance information detected by the impedance detection unit in order to determine high frequency energy applied from the different penetration depths of the high frequency needles.

17. A surgical navigation instrument comprising:

a needle module having a plurality of high frequency needles which are configured to be inserted into tissues to be treated;

a handpiece to which the needle module is coupled;
an impedance detection unit connected to electrodes of the high frequency needles through the handpiece, and configured to detect an impedance of the tissues while applying pilot signals for detecting impedance to the electrodes of the high frequency needles; and
a control unit connected to the needle module through the handpiece and configured to adjust the high frequency needles to have various penetration depths to the tissues according to setting signals input through a setting input unit so high frequency energies applied to the high frequency needles are controlled according to the impedance detected from the impedance detection unit,
wherein the setting input unit is a touch panel mounted on a surgical body, and displays a preset treatment mode and a manual treatment mode controlled by the control unit,
wherein the setting input unit in the manual treatment mode includes: a needle parameter setting button for setting treatment parameters of the high frequency needles; a treatment parameter setting button for allowing a user to select treatment parameters according to indications and treated areas; a shot number setting button for selecting the insertion number of the high frequency needles according to parameters set by the needle parameter setting button and the treatment parameter setting button; a parameter initialization button for restoring an initial value when treatment parameters of the high frequency needles and parameters set by the user are changed by the needle parameter setting button and the treatment parameter setting button; a suction on/off button for selecting activation and inactivation of a suction function; a needle cleaning button for maximizing forward movement of the high frequency needles in order to clean biological tissues attached to the high frequency needles during the treatment; and a suction pressure display unit for visually displaying the level of suction pressure in the range from 0% to 100% based on a threshold value in order to induce correction of a treatment posture and a treatment method in relation to the high frequency needles providing the suction function.

18. The surgical navigation instrument according to claim 17, wherein the control unit controls the high frequency needles to automatically move forwards when suction pressure displayed on the suction pressure display unit reaches the threshold value.

* * * * *